United States Patent
Fuchs et al.

(10) Patent No.: US 8,927,222 B2
(45) Date of Patent: Jan. 6, 2015

(54) METHOD FOR THE ISOLATION OF PROTEINS BINDING TO ANY KIND NUCLEIC ACID SEQUENCE OF INTEREST

(75) Inventors: Robert Fuchs, Marseilles (FR); Shingo Fujii, Marseilles (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 4 days.

(21) Appl. No.: 13/809,523

(22) PCT Filed: Jul. 5, 2011

(86) PCT No.: PCT/EP2011/003322
§ 371 (c)(1),
(2), (4) Date: Mar. 12, 2013

(87) PCT Pub. No.: WO2012/007117
PCT Pub. Date: Jan. 19, 2012

(65) Prior Publication Data
US 2013/0196326 A1   Aug. 1, 2013

(30) Foreign Application Priority Data

Jul. 13, 2010   (EP) .................................. 10007204

(51) Int. Cl.
G01N 33/53   (2006.01)
C12Q 1/68   (2006.01)
G01N 33/68   (2006.01)

(52) U.S. Cl.
CPC .......... *C12Q 1/6806* (2013.01); *G01N 33/6875* (2013.01); *G01N 2500/00* (2013.01); *C12Q 1/6813* (2013.01)
USPC ....................................................... 435/7.1

(58) Field of Classification Search
CPC .......... G01N 33/6875; G01N 2500/00; C12Q 1/6813; C12Q 1/6806; C12Q 1/6839; C12Q 2537/119
See application file for complete search history.

(56) References Cited

FOREIGN PATENT DOCUMENTS

WO   2009024781 A1   2/2009

OTHER PUBLICATIONS

Zahedi, Kamyar et al., "Normal Transcription of the C1 Inhibitor Gene Is Dependent Upon a Polypurine-Polypyrimidine Region Within the Promoter", Inflammation, vol. 26, No. 4, Aug. 2002, pp. 183-191.
Dejardin, Jerome et al., "Purification of Proteins Associated With Specific Genomic Loci", Cell, vol. 136, pp. 175-186, Jan. 2009.
Cassidy, Rachel A. et al., "Effect of DNA Target Sequence on Triplex Formation by Oligo-2'-Deoxy- and 2'-O-Methylribonucleotides", Nucleic Acids Research, vol. 31, No. 14, pp. 4099-4108, 2003.
Guilloneau, F. et al., "Selection and Identification of Proteins Bound to DNA Triple-Helical Structures by Combination of 2D-Electrophersis and MALDI-TOF Mass Spectrometry", Nucleic Acids Research, vol. 29, No. 11, 2001, pp. 2427-2436, 2001.
Agalioti, Theodora et al., "Ordered Recruitment of Chromatin Modifying and General Transcription Factors to the IFN-Beta Promotor", Cell, vol. 103, pp. 667-678, Nov. 2000.
Guieysse, Anne-Laure et al., "Psoralen Adducts Induced by Triplex-Forming Oligonucleotides Are Refractory to Repair in HeLa Cells", Journal of Molecular Biology, vol. 296, pp. 373-383, 2000.

*Primary Examiner* — James Martinell
(74) *Attorney, Agent, or Firm* — Browdy and Neimark, PLLC

(57) ABSTRACT

The invention is to supply a novel way for the isolation and identification of proteins bound to any kind of interesting nucleic acid sequence (Sequence-of-Interest: SoI), advantageously to any kind of interesting DNA sequence, particularly in the context of chromosomal DNA or RNA or episomal DNA in living cells or in test tubes.
In the context of the present invention, living cells include any organism that contains nucleic acid material as for example viruses, bacteria, cells, the bound protein of which have to be analyzed.
The invention is based upon the use of a specific nucleic acid sequence tag, advantageously a specific double-stranded DNA able to form triplex helix, referred to as the Triplex-Forming Tag sequence, (TFT sequence), that will be located nearby the SoI.

29 Claims, 3 Drawing Sheets

METHOD FOR THE ISOLATION OF PROTEINS BINDING TO ANY KIND NUCLEIC ACID SEQUENCE OF INTEREST

Eukaryotic DNA is bound and interpreted by numerous protein complexes in the context of chromatin.

A description of the full set of proteins that regulate specific loci is critical to understanding gene expression and regulation.

Cellular metabolisms, such as genome maintenance, gene expression, programmed cell proliferation, and so on, are archived (indexed) in chromatin by means of specific combinations of tightly regulated proteins that carry post translational modifications and are part of protein networks.

Despite substantial characterization efforts, chromosomes remain poorly characterized cellular organelles (Kornberg and Lorch, 2007).

Understanding the way transcriptional history is encoded and stored in chromatin is a huge challenge that is presently limited by the lack of convenient procedures to isolate specific fragments of chromatin, thereafter called Chromatin of Interest (CoI) and to analyze their protein content as a function of growth conditions, cell cycle, cell type, . . . .

The term "Chromatin•of•interest" fragment refers to the complex between a specific nucleic acid sequence (i.e. a given gene) and all the associated proteins.

Isolation of such specific nucleoprotein fragments is a particularly demanding task given the huge size of genomes such as the human genome ($3 \times 10^9$ bp).

To isolate a chromatin fragment associated to a single human gene (hypothetical average size of 3 kb), one will need to isolate 1 out of $10^6$ fragments.

There is a need for methods that simplify the isolation of CoI fragments.

During the past 25 years, various chromatin isolation strategies have been pursued to establish locus-specific protein composition.

While each achieved enrichment of the targeted region, none gave material in sufficient amount and purity to allow identification of bound factors.

Déjardin and Kingston (Cell 136, 175-186, Jan. 9, 2009) described a method based on Watson-Crick hybridization to isolate telomere containing chromatin fragments.

But this technique, can only be used for telomere fragments that contain single-stranded regions (3'-overhang) able to hybridize with complementary oligonucleotide probe by Watson-Crick base pairing.

Telomeres are an exception because (1) they naturally contain single strand DNA of known sequences that can thus form Watson-Crick base pairs with a complementary probe, (2) they are over-represented because there are 92 telomeres/cell.

The described technique is thus not universal and does not permit the isolation of nucleoprotein fragment outside the end of chromosomes, that is anywhere in the chromosome, more advantageously independently of the nucleic acid sequence of the fragments of interest.

There is a need for a method that permits to isolate nucleoprotein fragments of interest, located anywhere in a chromosome, advantageously chromatin fragments, and more advantageously independently of the nucleic acid sequence of the fragments of interest.

It is one of the aims of the present invention to propose such a method.

The invention is to supply a novel way for the isolation and identification of proteins bound to any kind of interesting nucleic acid sequence (Sequence-of-Interest: SoI), advantageously to any kind of interesting DNA sequence, particularly in the context of chromosomal DNA or RNA or episomal DNA in living cells or in test tubes.

In the context of the present invention, living cells include any organism that contains nucleic acid material as for example viruses, bacteria, cells, the bound protein of which have to be analyzed.

The invention is based upon the use of a specific nucleic acid sequence tag, advantageously a specific double-stranded DNA able to form a triple helix, referred to as the Triplex-Forming Tag sequence, (TFT sequence), that will be located nearby the SoI.

The invention is adapted to any source of nucleic acid (the SoI) in any kind of living cells as defined above, since a short triplex forming Tags (TFT) of a predetermined length, can be introduced nearby the said sequence of interest (SoI) and the proteins that are bound to it.

Advantageously, the invention is adapted to any source of DNA (chromosomal, episomal, viral . . . ).

According to the invention, the TFT sequence can be in the cells as part of an episomal DNA or integrated nearby the studied interesting nucleic acid sequence.

According to the invention, the TFT sequence can form a stable complex in the form of a triple helix with a specific oligonucleotide probe referred to as the Triplex Forming Oligonucleotide (TFO).

Whatever the final form of the TFT sequence (episomal or integrated), it can be under the form of a single sequence or of repeated sequences. When it is under the form of repeated sequences, the repeated sequences can be arranged head to head or head to tail, contiguously or spaced.

Thus according to the invention, the first step of the method is to introduce a TFT sequence nearby the SoI the complexed proteins of which will be analyzed.

When the TFT is introduced in the vicinity of the SoI, the SoI and its associated proteins can be purified from a complex mixture of unrelated nucleic acid fragments by the use of the TFO probe.

Thus, a first object of the invention relates to a new method for the isolation of the proteins bound to any kind of interesting nucleic acid sequence (Sequence-of-Interest: SoI), wherein in a first step a Triplex Forming Tags (TFT) is introduced in said nucleic acid sequence of a living cell and said living cells are grown;

in a second step cells obtained in step 1 are collected and mixed with a molecular probe specific of the introduced TFT (the TFO probe) in conditions that permit the formation of nucleic acid triplex;

in a third step the nucleic acid triplex formed in second step are isolated and bound proteins are analyzed.

According to the invention, interesting nucleic acid sequence (SoI) is used to name the nucleotide sequence that will be isolated with the method according to the invention. Using this expression does not prejudge the fact that the sequence was known beforehand or not.

According to the invention, the method can be applied to prokaryotic or eukariotic cells.

According to the invention, interesting nucleic acid sequence (SoI) can be DNA (Deoxyribonucleotide acids) or RNA (ribonucleotide acids), advantageously DNA, more advantageously genomic nucleic acid (DNA or RNA), preferably genomic DNA or episomal DNA.

According to the first step of the invention, the TFT can be part of double strand linear or circular nucleic acid (the TFT containing nucleic acid), preferably double stranded linear or circular DNA.

In one first embodiment of the invention, the TFT containing nucleic acid can be maintained in the cell as an episome. According to this embodiment the TFT containing nucleic acid will be a circular nucleic acid, preferably a plasmid including in addition to the TFT sequence a viral origin.

In a second embodiment of the invention, the TFT containing nucleic acid can be introduced in said nucleic acid sequence randomly or in a directed manner that is introduced close to a predetermined SoI. When the TFT containing nucleic acid insertion is made at random it will be possible to analyze unknown SoI. For this the TFT containing nucleic acid can be any type of DNA, advantageously further comprising a reporter sequence used as a marker for the detection of cells having said integrated DNA.

When the TFT containing nucleic acid insertion is made in a directed manner via either homologous or site-specific recombination, it will be possible to analyze a known SoI and the protein bound on it. The insertion of the TFT containing nucleic acid will be in an area of known nucleic acid sequence of interest whose flanking sequences are known that allows introducing specifically the TFT containing nucleic acid nearby the known SoI to be analyzed. In this embodiment the TFT containing nucleic acid will be preferably as a plasmid including in addition to the TFT sequence known flanking sequences that will permit homologous recombination between the plasmid and the nucleic acid of interest. One more it can be an advantage that said plasmid further comprises a sequence used as a marker for the detection of cells having said integrated DNA.

According to the first step of the invention, the nucleic acid containing the Triplex Forming Tags (TFT containing nucleic acid) can be introduced in said living cell through any known methods such as the calcium phosphate method (Graham, F. L. and Van Der Eb., A. J., 1973, Virology 52:456-467), the DEAE dextran method (Farber, F., et. al., 1975, Biochem. Biophys. Acta., 390:298-311; Pagano, J. S., 1970, Prog. Med. Virol. 12:1-48), the polyornithine method (Farber, F., et. al., 1975, Biochem. Biophys. Acta., 390:298-311), the DNA microinjection method (Cappechi, M. R., 1980, Cell. 22:479-488), the polyethylene glycol (PEG)/dimethylsulfoxide (DMSO) method (Jonak, Z. L., et. al., 1984, Hybridoma 3:107-118), the trypsin/EDTA/glycerol (Chu, G. J. and Sharp, P. A., 1981, Gene 13:197-202), the osmotic shock method (Okada, G. Y., and Rechsteiner, M., 1982, Cell 29: 33-41), a liposome fusion method (Poste, G., et. al., 1976, Methods. Cell. Biol., 14:33-71; Fraley, R. et. al., 1980, J. Biol. Chem. 255; 10431-10435; Wong, T. K., et. al., 1980, Gene 10; 87-94), the ghost red cell mediated method (Furusawa, M., et. al., 1976, Methods. Cell. Biol., 14: 73-80; Straus, S. and Raskas, H., 1980, J. Gen. Virol. 48: 241-245; Godfrey, W., et. al., 1983, Proc. Natl. Acad. Sci. U.S.A. 80: 2267-2271), the bacterial protoplast fusion method (Chu, G. J. and Sharp, P. A., 1981, Gene 13:197-202; Sandri-Goldin, R. M., et. al., 1981, Mol. Cell. Biol. 1:743-752; Oi, V. T., and Morrison, S. L., 1986, Biotechniques 4: 214-221), the reconstituted Sendai virus envelope method (Loyter, A., et. al., 1984, Ciba. Found. Symp., 103:163-180), the laser-beamporation (Tsuka koshi, M., et. al., 1984, Appl. Phys. B., 35: 2284-2289; Tao, W., et. al., 1987, Proc. Natl. Acad. Sci. U.S.A. 84: 4180-4184), the electroporation method (Neumann, E., et. al., 1982; EMBO. J., 1:841-845; Potter, H., et. al., 1984, Proc. Natl. Acad. Sci. U.S.A. 81: 7161-7165), the tungsten microprojectile method (Klein, T. M., et. al., 1987, Nature 327: 70-73), the retrovirus vector method (Jaenisch, R., 1976, Proc. Natl. Acad. Sci. U.S.A., 73: 1260-1264: Jahner, D. and Jaenish, R., 1980, Nature 287:456-458).

According to the preferred embodiment of the invention, that is the TFT containing nucleic acid integration in the nucleic acid sequence, the use of techniques such as homologous recombination or site-specific recombination are preferred. Such techniques are well known in the art. According to the invention the technique described by Sorrell D A and Kolb A F., ("Targeted modification of mammalian genomes" Biotechnol Adv. 2005 November; 23(7-8):431-69) is preferred.

According to the first step of the invention, living cells can be grown according to any known culture method as long as the method is appropriate to the used living cells. One skilled in the art will have no difficulty to find the good culture conditions appropriate to the cells he is studying.

According to the invention the TFT sequence will have to be recognised by a molecular probe specific of it and will have to form a stable complex in the form of a triple helix with said specific molecular probe referred to as the Triplex Forming Oligonucleotide (TFO).

Generally speaking according to the invention, in the first step, the Triplex Forming Tags (TFT) can be any nucleic acid sequence that can be used as Tag, with the condition that its sequences is known and a complementary specific molecular probe can be prepared.

In another embodiment of the invention, which is the preferred one, the TFT sequence can be a sequence that is usually not present in the nucleic acid sequence in which the SoI is present.

Many studies have been performed on the specificity of TFT. According to these studies, structural requirements influence the design of TFOs and have lead to the classification in different subtypes with individual binding properties of the specificity head of the TFO that is the specific molecular probe that recognise the TFT.

Triplex-forming oligonucleotides (TFOs) bind in the major groove of oligopyrimidine-oligopurine sequences allowing specific targeting of the double-stranded DNA.

It is known that most of the time DNA exists as a duplex formed by anti-parallel chains hold together via the Watson-Crick base pairing scheme: A/T, G/C.

But it is also known that DNA duplexes containing Poly-Purine (poly-Pu) tracks in one strand (and poly-Pyrimidine (poly-Py) tracks in the complementary strand) are able to form triplexes with either poly-Py or poly-Pu oligonucleotides by means of Hoogsteen base pairs.

Thus in another preferred embodiment of the invention, the TFT sequence can be a poly-pyrimidine-poly-purine sequence, that is a sequence that can be recognised via Hoogsteen base pairs by a poly-pyrimidine TFO or a poly-purine TFO.

Preferably the TFT sequence can be a poly-pyrimidine-poly-purine sequence that can be recognised via Hoogsteen base pairs by a poly-pyrimidine TFO.

In a best preferred embodiment the TFT sequence can be a poly-pyrimidine-poly-purine sequence that is usually not present in the nucleic acid sequence in which the SoI is present.

According to the invention, the TFT sequence can have a length comprised between 10 to 50 base pairs, preferably between 15 to 35 base pairs very preferably of about 20 base pairs long.

According to the second step of the method of the invention, said cells obtained in step 2 are collected and mixed with a molecular probe specific of the introduced TFT (the TFO probe) in conditions that permit the formation of nucleic acid triplex.

According to the second step of the invention cells can be collected according to any known method such as for example methods as described in Molecular cloning: a laboratory manual; (Joseph Sambrook, David William Russell, Cold Spring Harbor Press, Cold Spring Harbor, N.Y., 2001). Preferably cells are collected by scraping and centrifugation.

At this step as the collected cells generally form a more or less compact cluster, it may be worthwhile to add a fragmentation step before adding the TFO probe. In this way many mechanical (shearing methods), enzymatic or sonic techniques can be used. Sonication methods are preferred according to the invention.

This fragmentation step can improve the following step of triplex formation between the TFO probe and the TFT sequence.

According to the second step of the invention, once collected, eventually fragmented, cells have to be put in contact with a TFO probe in a way that facilitates the recognition of the TFT sequence by the TFO. Any method that leads to the triplex formation between the TFO probe and the TFT sequence can be used according to step 2 of the method of the invention.

In one preferred embodiment of this second step of the invention the recognition of the TFT sequence by the TFO can be facilitated in purifying or isolating the cells' nuclei prior to mixing it with the TFO. By purifying or isolating the nuclei it should be understood that said collected cells are subjected to treatment such as their nucleic acids and proteins or eukaryotic cell nuclei are at least partially isolated from their cellular environment. The skilled person knows many techniques to achieve such a result. Such techniques are well described in the literature of biology and/or molecular biology.

According to the invention the collected cells can be lysed and nucleic acids and proteins or eukaryotic cell nuclei can be then purified or isolated. One of the preferred method to attempt this result can be the method as described in Molecular cloning: a laboratory manual (Sambrook J. and Russell D., Cold Spring Harbor Laboratory Press, U.S.; third edition (Dec. 5, 2000)).

According to the invention, the TFO probe can be any nucleic acid sequence, complementary to the inserted TFT sequence, alone or combined with other elements that increase its effectiveness.

It has been reported that stabilization of triplex formation and high recognition specificity of a selected target site (Triplex Forming Tag site) can be achieved by the following modifications of the TFO probe:

1—Introduction of locked nucleic acids (LNA) nucleotides mixed with normal nucleotides: Locked Nucleic Acids (LNA) comprises ribonucleotides with a 2'-O,4'-C-methylene linkage. LNA-containing TFOs have been recently described to effect very significant triplex stabilization. More precisely, previous works have thus shown that alternating LNA and normal nucleotides in TFO sequences is appropriate for triplex formation. Thus according to the invention, the TFO can comprise preferably nucleic acids (LNA) nucleotides mixed with normal nucleotides (Alexei A. et al., (1998). "LNA (Locked Nucleic Acids): Synthesis of the adenine, cytosine, guanine, 5-methylcytosine, thymine and uracil bicyclonucleoside monomers, oligomerisation, and unprecedented nucleic acid recognition". *Tetrahedron* 54 (14): 3607-30; Satoshi Obika et al. (1998). "Stability and structural features of the duplexes containing nucleoside analogues with a cross-linked N-type conformation, 2'-O,4'-C-methyleneribonucleosides". *Tetrahedron Lett.* 39 (30): 5401-4).

2—Addition of a chemical compound composed by any aromatic ring structure working as an intercalator at the 3' or 5'-end of TFO. Such aromatic ring structure can be for example psoralen, acridine, ethidium bromide, berberine, proflavine, daunomycin, doxorubicin, thalidomide, quinacrine, or orthophenanthroline.

3—Replacement of cytosine by 5-methyl cytosine.

Thus according to one preferred embodiment of the invention, the TFO can be a nucleic acid sequences comprising locked nucleic acid (LNA) nucleotides mixed with normal nucleotides.

In another preferred embodiment of the invention, the TFO can comprise at its 3' or 5'-end a chemical compound composed by any aromatic ring structure, for example an intercalating agent such as psoralen, acridine, ethidium bromide, berberine, proflavine, daunomycin, doxorubicin, thalidomide, quinacrine, or orthophenanthroline, preferably psoralen. Preferably said chemical compound can be a photo-activable compound, most preferably a photo-activable intercalating agent. This will permit, once the chemical compound is intercalated into the double stranded TFT nucleic acid, to covalently link said compound to the nucleic acid, using a photon emissive source. This will reinforce the strength of the TFO/TFT complex thus facilitating the recovery of the Protein/nucleic acid complex in the final purification step.

In another preferred embodiment of the invention, in the TFO cytosines can be replaced by 5-methyl cytosine.

In one of the very preferred embodiment of the invention the TFO can be a nucleic acid sequences comprising locked nucleic acids (LNA) nucleotides mixed with normal nucleotides, that can comprise at its 3' or 5'-end an aromatic ring structure, for example an intercalating agent and in which cytosines can be replaced by 5-methyl cytosine.

In another embodiment of the invention, the TFO probe can comprise a specificity head as described above (LNA and normal nucleotides, namely the probe, with an aromatic ring structure at one of its 3' or 5'-end) followed at its opposite end) 3' or 5') end by a linker connected to a capture handle that can be specifically captured by a cognate capture hook.

According to the invention, said linker can be of any type of known spacers, preferably a carbon spacer that can have a length comprised between 1 to 300 carbon atoms, preferably between 100 to 200, most preferably between 110 to 130 carbon atoms.

According to the invention, the capture device (capture handle/cognate capture hook) can be any couple of strongly interacting molecules, such as for example any kind of materials showing affinity interaction such as, combination of histidine-metal, antigen-antibody (e.g., FLAG-anti FLAG), specific oligonucleotide-specific oligonucleotide binding protein (e.g., lacO-LacI), and so on.

In a particular embodiment the capture handle can be a compound that can bind to another one used as a hook. Preferred hook can be streptavidin or an equivalent such as Avidin or Neutravidin and preferred capture handle can be biotin or equivalent such as desthiobiotin.

According to a very preferred embodiment the TFO probe can be designed from its 5' end as an intercalating agent (psoralen) linked to the TFO sequence linked to a spacer linked to a capture handle.

FIG. 1 shows an example of such a TFO probe.

In the second step of the method of the invention, a nucleotide Triplex structure has to be formed. Any conditions that permit such a formation can be used according to the invention. One of the preferred methods that can be used according to the invention is the one described in Brunet et al. (Nucleic Acid Research, 2005, Vol. 33, N.° 13, 4223-4234).

According to the third step of the method of the invention, the nucleic acid triplex formed in second step can be isolated according to any known methods. Preferred method can be a method in which a hook, specific to the capture handle, is used to bind to the capture handle. Such methods can be for example combination of histidine-metal, antigen-antibody (e.g., FLAG-anti FLAG), specific oligonucleotide-specific oligonucleotide binding protein (e.g., lacO-LacI) with the condition that.

According to one of the preferred embodiment of the invention where the capture handle is a biotin or an equivalent, the hook can be a streptavidin.

To facilitate the purification of the captured triplex the hook can be fixed on a column or on beads, for example magnetic beads. The use of the magnetic beads is the preferred purification method used according to the invention. Such methods are described in many references such as Déjardin and Kingston (Cell 136, 175-186, Jan. 9, 2009).

According to a specific alternative form of the invention, a cross-linking step of the proteins bound to the nucleic acid can be added to the method. This cross-linking step can be added just after step 1 that is before the collecting step or can be added just after the collection of the cells that is just before adding the TFO probe.

This step can be of importance because during cross-linking the proteins surrounding the nucleic acid are cross-linked between-them and between them and said nucleic acid.

According to the invention, any method known in the art that permits the protein-protein and/or protein-nucleic acid crosslink can be used as for example for Protein-DNA crosslink: UV photo crosslinking, formaldehyde cross-linking technique, Hexavalent chromium and for Protein-Protein for further analysis by combined with Protein-DNA crosslink: dimethyl adipimidate (DMA); disuccinimidyl suberate (D88); dithiobis[succinimidyl propionate] (D8P); ethylene glycolbis[succinimidyl succinate] (EG8).

Preferably the in vivo formaldehyde cros-linking technique can be used according to the method described by Orlando V et al. (Methods. 1997 February; 11 (2):205-14).

It is noteworthy that the cross-linking step can be not necessary, if the interactions between proteins or between proteins and nucleic acids are strong enough so that it is not necessary to conduct an additional cross-linking step.

According to another specific alternative form of the invention, to optimize the method a cell lysis step can be added to the method. According to which embodiment of the invention is chosen (with or without cross-linking step), this cell lysis step can be added at different times in the method of the invention.

When no cross-linking step is performed according to the method, this cell lysis step can be added once the cells have been collected in the second step of the method.

When a cross-linking step is performed according to the method, this cell lysis step can be added indifferently before or after the cross-linking step, preferably before.

Notwithstanding the embodiment of the method used (with or without cros-linking step), the cell lysis step can be performed as according any known manner, preferably according to the method described in the following references. ("Association of RNA polymerase with transcribed regions in Escherichia coli", Wade J T, and Struhl K.; Proc Natl Acad Sci USA. 2004 Dec. 21; 101(51):17777-82 or "Cockayne syndrome A and B proteins differentially regulate recruitment of chromatin remodeling and repair factors to stalled RNA polymerase II in vivo", Mol Cell. 2006 August; 23(4):471-82).

The invention also relates to the use of the method of the invention for the preparation of nucleotide-protein complex.

The invention finally relates to a kit for the implementation of the method of the invention, said kit comprising at least one TFT to be introduced near the SoI in the nucleic acid sequence of a living cell said TFT being as described previously in the present text, at least one cross-linking compound, at least one molecular probe specific of the TFT sequence (the TFO probe), said TFO probe being as described previously in the present text, and a hook constituted by a compound that can bind to the TFO's capture handle.

The present invention will be better understood, and its details more clearly apparent, on reading the following example and description in relation to the figures described in the section below.

The recovered samples are analyzed by agarose gel electrophoresis. Estimation of plasmid recovery compared to input is: pAS03, <1%; pAS03.1, 53%; pAS03.2, 60%; pAS04, 67%. Plasmids used in the present experiment are amplified and purified from E. coli. CC: closed circular. OC: open circular. Dimer: dimerized plasmid.

Figure 4:
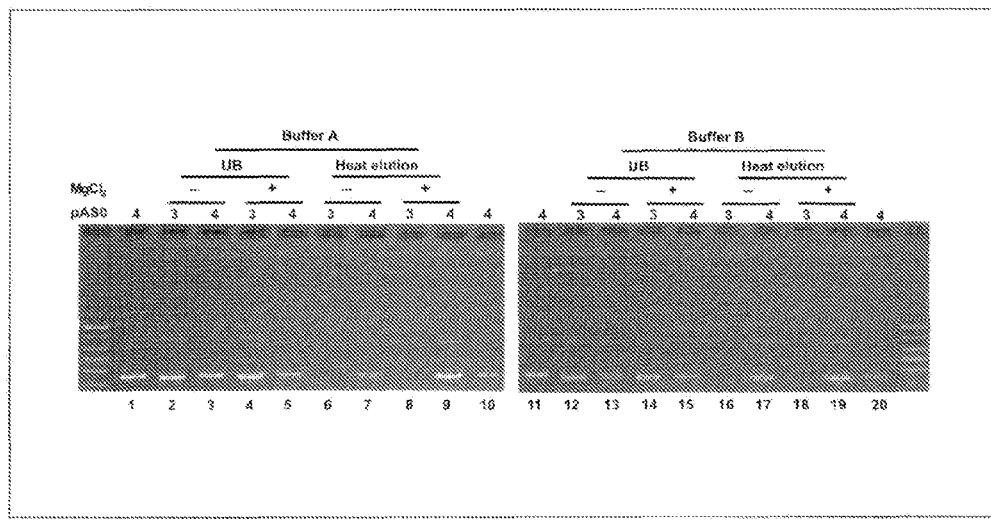

FIG. 4: shows the plasmid isolation via TFO-1 under different buffer conditions in vitro. Each 400 ng (≈93 fmol) of plasmids (pAS03, pAS04) are mixed with 8 pmol of TFO-1 (final 0.4 µM) and are agitated for 11 hr. 150 µg of C1 are added into the mixture and are agitated for 2 hr. The mixture is placed on a magnetic stand and supernatant is removed (this supernatant is referred to as Unbound fraction).

The collected C1 fraction is washed twice and plasmid captured on the C1 is released by boiling. The recovered samples are analyzed by agarose gel electrophoresis. If plasmid is recovered thoroughly, unbound fractions (UB, lanes 2-5, 12-15) and plasmid eluted from C1 (Heat elution, lanes 6-9, 16-19) are loaded with 15 ng and 20 ng equivalents of plasmids, respectively.

Lanes (1, 11) and lanes (10, 20) are loaded with 15 ng and 5 ng of pAS04 as a control, respectively, Buffer A is composed of 12.5 mM Tris-HCl (7.6), 75 mM NaCl, 0.5% NP-40, 0.5% Sodium deoxycholate, 0.05% SDS, 0.1 mM EDTA, 0.5 mM EGTA, 0.1% Sarkosyl, and with/without 10 mM $MgCl_2$. Buffer B is composed of 25 mM Tris-HCl (7.6), 150 mM NaCl, 1% NP-40, 1% Sodium deoxycholate, 0.1% SDS, 0.1 mM EDTA, 0.5 mM EGTA, 0.1% Sarkosyl, and with/without 10 mM $MgCl_2$.

Figure 5:
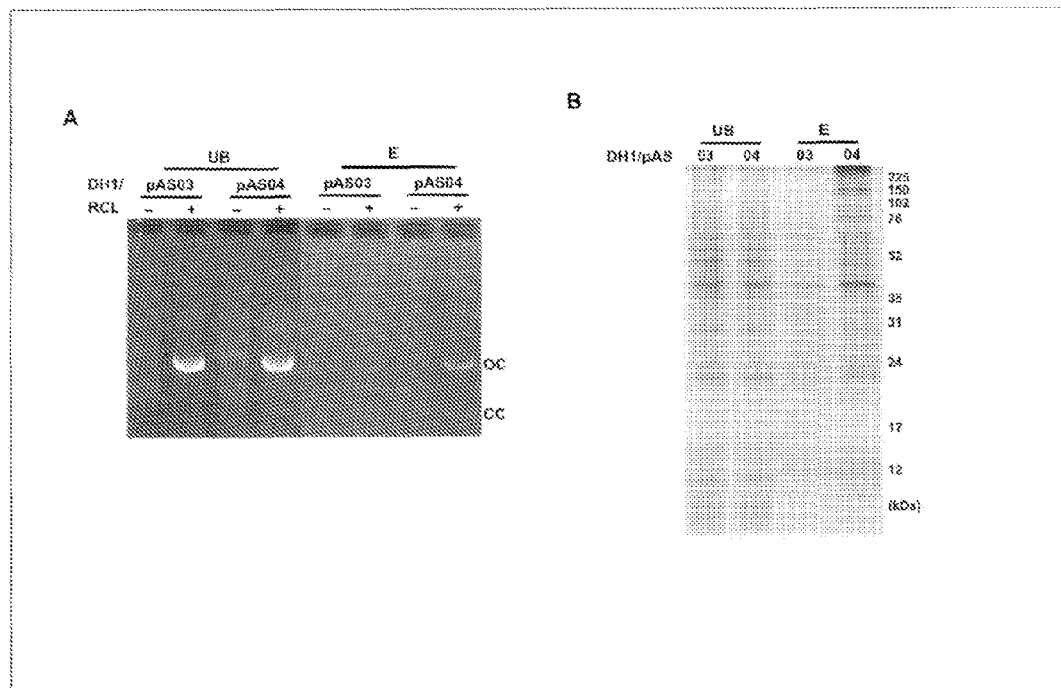

FIG. 5: shows the isolation of plasmid and proteins bound to plasmids recovered from *E. coli*. DH1/pAS03 or DH1/pAS04 strains are grown to $OD_{600}$=0.4. Cells are crosslinked by formaldehyde treatment (final 3%) for 30 min, disrupted and treated with RNaseA. Soluble fraction (sup-1) is separated from the insoluble fraction by centrifugation. The insoluble fraction is resuspended and sonicated in order to further solubilize material (sup-2). The combined soluble fraction sup-1 plus sup-2 are mixed with C1 in order to remove proteins that can bind to C1 beads independently of the presence of TFO-1. The recovered supernatant is used as the input for the TFO approach. Aliquot of the mixture ($7\times10^7$ cells equivalent from 1.75 ml culture at $OD_{600}$=0.4) are mixed with 12.5 pmol of TFO-1 (final 0.25 µM) and are agitated for 18 hr. 200 µg of C1 are added to the mixture and are agitated for 2 hr. The mixture is placed on a magnetic stand and supernatant is removed (this supernatant is referred to as Unbound fraction (UB). The collected C1 is washed 6 times and plasmid captured on the C1 is released by addition of buffer containing 10 mM biotin (this eluted sample is referred to as Elution fraction (E)).

A) The recovered samples (UB and E) are reverse crosslinked (RCL) by heat or not, and 3.3% (UB) and 10% (E) of samples are analyzed by agarose gel electrophoresis.

Figure 6:
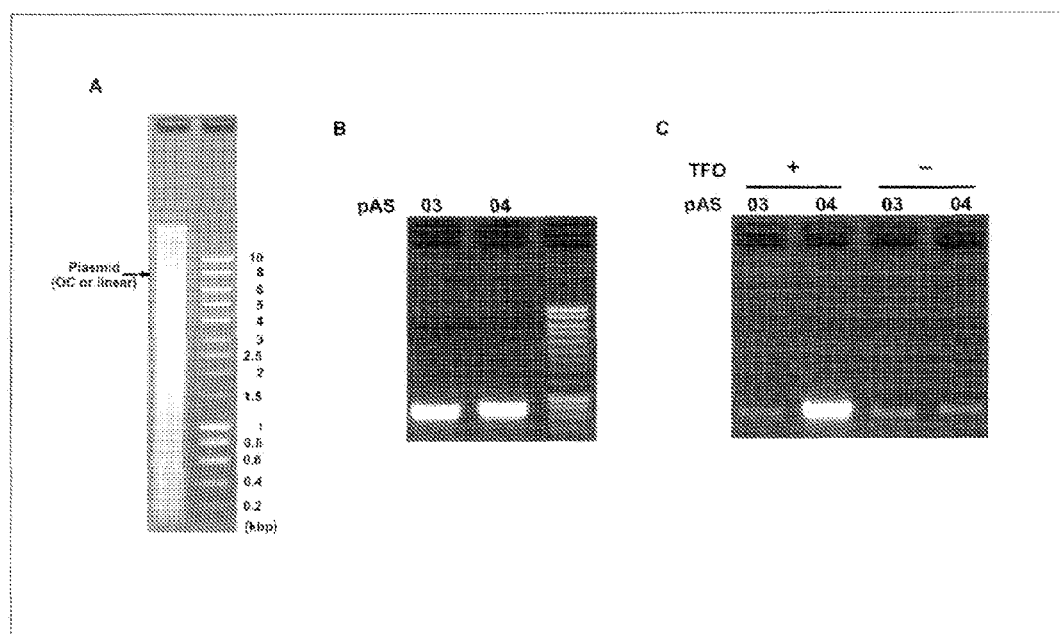

B) 0.1% (UB) and 20% (E) of samples are reverse crosslinked and analyzed by silver staining following SDS-PAGE FIG. 6: shows the isolation of plasmid recovered from human cell lines. The supernatant is mixed with streptavidin-conjugated beads in order to remove the intrinsically biotinylated proteins present in human cells.

The recovered supernatant (S) is used as the input for the TFO approach. Aliquot of the S containing ≈3 µg of total DNA (plasmid DNA: ≈4.5 ng) are mixed with 2.5 pmol of TFO-1 (final 0.25 µM) and are agitated for 16 hr. 40 µg of C 1 are added to the mixture and are agitated for 16 h. The collected C1 is washed 7 times and plasmid captured on the C1 is released by addition of buffer containing 10 mM biotin (this eluted sample is referred to as Elution fraction (E). Before PCR analysis, all samples are treated for crosslink reversal by heat and deproteination.

A) 500 ng of DNA of the supernatant are analyzed by agarose gel electrophoresis. A weak band corresponding to the size of linear or open circular plasmid DNA can be distinguished.

B) 1 ng of DNA of S derived from either pAS03 or pAS04 are used as templates for PCR amplification using primers that encompass the TFT-1 site; the amplified fragments, 670 and 731 by for pAS03 and pAS04 respectively, are analyzed by agarose gel electrophoresis.

C) 1% of samples recovered after elution of the beads (E) are used as templates for PCR and analyzed by agarose gel electrophoresis.

EXAMPLE 1

Construction of the Triplex Forming Oligonucleotide Probe (TFO Probe)

Figure 1:
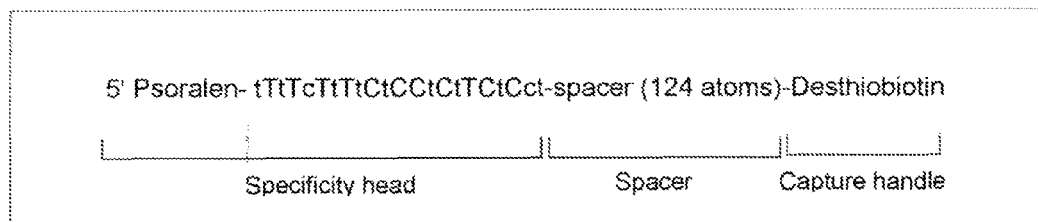
FIG. 1: shows an example of one possible TFO probe (TFO-1): the specificity head is formed by a modified 22-mer oligonucleotide (SEQ ID NO:1) composed of a mixture of LNA and DNA residues in small and capital letters respectively. Capital C represents 5-methyl cytosine residues; a psoralen residue is grafted at the 5'-end of the oligonucleotide. Its 3'-end is modified with a desthiobiotin residue (the capture handle) attached to spacer composed of a linear chain of 124 atoms.

According to the invention and as shown in FIG. 1, the final construction of the TFO-1 probe possesses the following features:

1—A psoralen residue attached at the 5'-end of the oligonucleotide via a six carbons spacer;

2—The 22-mer sequence specific oligonucleotide in which 11 residues are substituted by LNA (small letters) and all cytosine residues including cytosine-LNA analogues are substituted by 5-methyl cytosine;

3—Desthiobiotin (biotin analogue) instead of biotin is conjugated at 3'-end of oligonucleotide via a 124 atoms spacer.

The use of desthiobiotin instead of biotin is justified by its weaker affinity to streptavidin, allowing desthiobiotin-streptavidin interactions can be displaced by addition of free biotin.

EXAMPLE 2

Construction of Plasmid DNA Containing Triplex Forming Tags (TFT)

Plasmid, pAS03 (6290 bp), is derived from pcDNA3.1(+) CAT (6217 bp, Invitrogen) by modification of several restriction endonuclease recognition sites.

Figure 2:
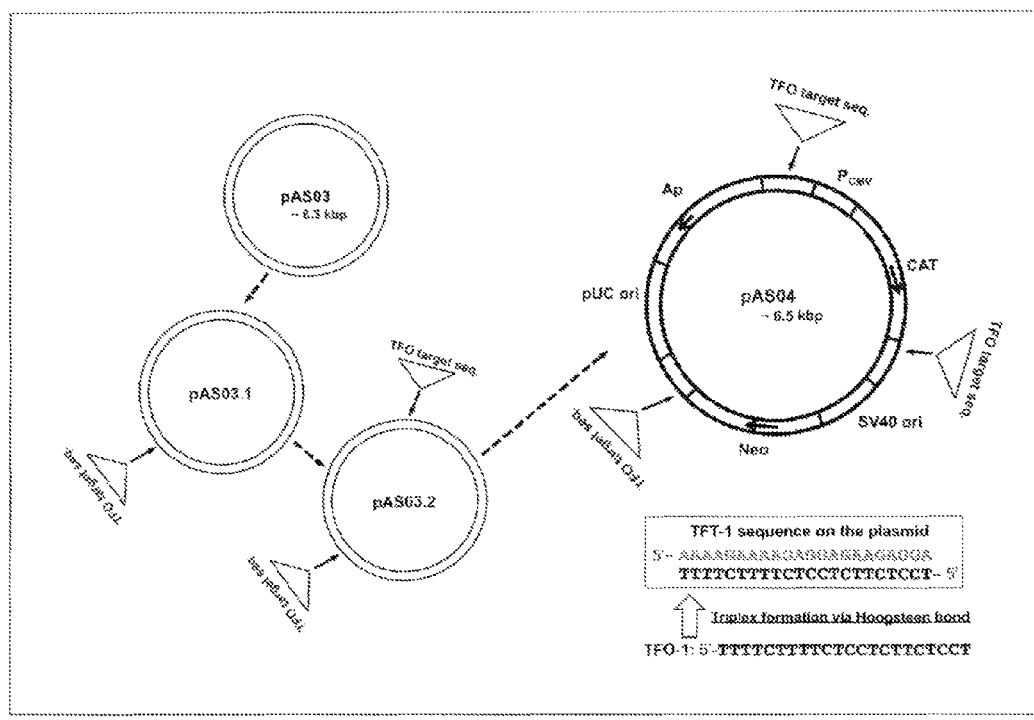
FIG. 2: shows the construction of plasmids containing Triplex Forming Tag (TFT) sequence (SEQ ID NOs: 1 and 2): pAS03 is derived from pcDNA3.1(+)CAT (Invitrogen). pAS03.1 is derived from pAS03 by inserting the TFT-1 sequence. pAS03.2 is derived from pAS03.1 by inserting an additional TFT-1 sequence. pAS04 is derived from pAS03.2 by inserting a third TFT-1 sequence. The TFT-1 sequence in red forms a triplex with the TFO-1 probe via Hoogsteen bond. pUC ori: high copy number origin in E. coli. SV40 ori: replication origin in primate cells expressing SV40 large T antigen. Ap: ampicillin resistance gene. Neo: neomycin resistance gene. CAT: chloramphenicol resistance gene, PCMV: human cytomegalovirus immediate-early promoter/enhancer.

One to three TFT-1 sequences, that form triplexes with TFO-1 as described in example 1, are introduced into pAS03, The resulting plasmids are named pAS03.1 (one TFT-1 sequence), pAS03.2 (two TFT-1 sequences) and pAS04 (three TFT-1 sequences, 6473 bp) (FIG. 2).

As these newly constructed plasmids retain ColE1 and SV40 origins, they can be amplified in *E. coli* and cultured in primate cells expressing SV40 large T antigen.

FIG. 2 is a map of the constructed plasmids.

EXAMPLE 3

TFO-Mediated Plasmid Capture in vitro

In order to verify that the TFO-1 probe recognizes efficiently the TFT-1 sequences in plasmid DNA, the plasmids prepared in example 2 are mixed with the TFO-1 probe and agitated.

Dynabeads MyOne Streptavidin C1 (Invitrogen) magnetic beads (C1) are added to the mixture and are further agitated.

The mixture is, thereafter, exposed to a magnetic stand to separate C1-bound fraction from unbound fraction. Following sample rinsing of the C1 fraction to remove non-specific binding of plasmid DNA, the C1 beads are eluted by heat or by the addition of free biotin.

The eluted products are analyzed by agarose gel electrophoresis.

Figure 3:
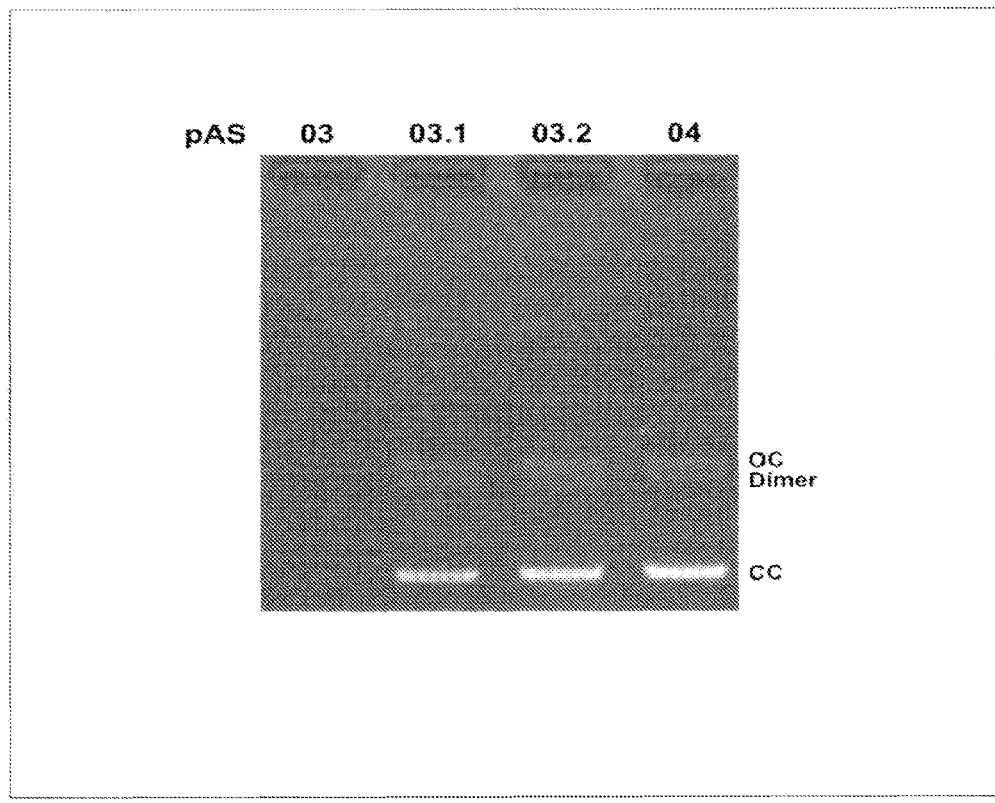
FIG. 3: shows the results obtained in example 3 for the plasmid isolation via TFO-1 in vitro. For each plasmid (pAS03, pAS03.1, pAS03.2, pAS04) 600 ng (≈140 fmol) are mixed with 8 pmol of TFO-1 (final 0.4 µM) and are agitated for 24 hr. 150 µg of C1 are added to the mixture and agitated for 18 hr. The mixture is placed on a magnetic stand and the C1-bound fraction is collected. The collected C1 is washed twice and plasmid captured on the C1 is released by boiling.

As shown in FIG. 3, plasmids are recovered depending on the presence of the TFT-1 sequence. The data clearly showed the high specificity and stability of the complex between TFO-1 and TFT-1 sites. Based on titration (amounts of TFO-1, C1, and plasmid) and time course (agitation time of plasmid with TFO-1, plasmid/TFO-1 with C1, and elution for plasmid/TFO-1 from C1) experiments, it can be concluded the following conclusions:

1. A molecular ratio of about 10:1 of TFO-1 to plasmid (e.g. pAS04) is optimal to achieve efficient recovery of the plasmid. This ratio is effective over a large TFO-1 concentration range (e.g. around 40 nM~1000 nM);
2. Non-specific capture of pAS03 (no TFT-1 sequence) by TFO-1 is less than 0.2% of input;
3. 20 µg of C1 beads capture around 94 ng of pAS04 via TFO-1;
4. Around 1 pmol of TFO-1 is the ideal amount when using 20 µg of C1;
5. Incubation time between plasmid and TFO-1: 2~3 hours (hr) at room temperature (RT) is enough while a longer incubation time (e.g. over 12 hr) is slightly better;
6. Incubation time between plasmid with TFO-1 and C1 beads: 1.5-2 hr at RT is enough while a longer incubation time (e.g. over 12 hr) is slightly better;
7. Nearly maximum elution of the TFO-1-plasmid complex from the C1 beads is achieved by addition of free biotin, for 3 hr at RT.

EXAMPLE 4

Buffer Components

For the purpose of isolating proteins using the present methodology, the buffer requires the presence of mild detergents in order to dissolve crosslinked DNA-protein complexes.

The TFO-mediated plasmid isolation in vitro, as described in example 3, were tested under different buffer conditions including detergents and found the recovery yield of plasmid to be decreased by lower ionic strengths. These effects can be counteracted by the addition of $MgCl_2$ (FIG. 4).

In conclusion, the TFO-plasmid capture approach is functional in buffers including detergents, the addition of $MgCl_2$ improving the signal over noise ratio.

EXAMPLE 5

Isolation of Plasmids and Plasmid-Protein Complexes from *Escherichia coli*

To check the feasibility of the TFO procedure, i.e. its capacity to isolate proteins bound to a specific DNA sequence containing a TFT sequence in a living organism, experiments involving *E. coli* strains were first implemented.

*Escherichia coli* DH1 strain is transformed either with pAS03 or pAS04 and the transformed strains are used as model strains.

Cells from strains DH1/pAS03 and DH1/pAS04 are grown to $OD_{600}$=0.4 in liquid and crosslinked by formaldehyde treatment (final 3%) for 30 minutes (min) at RT.

Crosslinked cells are disrupted and subjected to treatment with RNaseA to digest the RNA fraction.

The soluble fraction (sup-1) is separated from the insoluble fraction by centrifugation.

The insoluble fraction is re-suspended in a buffer and sonicated in order to recover an additional fraction of soluble material (sup-2).

The mixture sup-1 plus sup-2 is used as the material for the isolation of plasmid-protein complexes by the TFO approach.

As shown in FIG. 5A, pAS04 is specifically isolated. Although a significant amount of plasmid is observed in the fraction that did not bind to C1 beads (unbound fraction UB), the unbound plasmid can be recovered by a second cycle of TFO capture.

Compared to the in vitro reaction where 20 µg of C1 had the capacity to capture around 94 ng of pAS04, the present experiment involving *E. coli* crude extract, 20 µg of C1 captured only around 10 ng of pAS04.

Whenever necessary, the recovery yield can be compensated by a corresponding increase in the amount of C1 beads.

As shown in FIG. 5B, the amount of proteins recovered from DH1/pAS04 is significantly higher compared to DH1/pAS03. These results show that proteins associated to plasmid in vivo can be specifically recovered from crude *E. coli* extracts by the present TFO approach.

EXAMPLE 6

Isolation of Plasmid from Human Cells

As a next step the TFO procedure has been adapted to the capture of plasmid DNA in human cells.

The human cell line, 293FT (Invitrogen), is transiently transformed either with pAS03 or pAS04 and the transfected cells are used as model strains to investigate the feasibility of the TFO approach in human cells.

The cells are crosslinked by formaldehyde treatment (final 3%) for 30 min at RT. Nuclei are isolated from the crosslinked cells and are subjected to treatment with RNaseA to digest the RNA fraction. The nuclei are disrupted by sonication and soluble fraction (supernatant; sup) is separated from the insoluble fraction by centrifugation.

The average chromosomal DNA fragment size in the supernatant is around 3-4 kbp (FIG. 6A), a size close to the original plasmid size (≈6.5 kbp). Indeed full-length plasmid, in its linear or open circular (OC) form, can barely be distinguished within the DNA smear on the agarose gel (FIG. 6A) when 500 ng of DNA of the supernatant are analyzed. It should be noted that the quality of the supernatant preparation is critical).

The supernatant is mixed with streptavidin-conjugated beads in order to remove the biotin-containing proteins present in human cells. The supernatant (S) is used as the material for the isolation of plasmid-protein complexes by the TFO approach. In order to quantify the amount of plasmid DNA in S, amplification of the plasmid DNA fragment by PCR is implemented.

As shown in FIG. 6B, both pAS03 and pAS04 plasmid DNA are similarly amplified and are estimated to represent ≈0.15% of total DNA in S. A starting quantity of S containing ≈3 µg of total DNA (i.e. estimated amount of plasmid DNA: ≈4.5 ng) is first mixed with 2.5 pmol of TFO-1, then with 40 µg of C1. We then added an excess of single stranded DNA (10 µM final concentration of 19-mer oligonucleotide) in order to prevent non-specific binding of DNA and DNA/protein complexes on the surface of C1 (bead passivation process). After washing the C1 beads, plasmid DNA captured on the C1 beads is released and analyzed by PCR. As shown in FIG. 6C, pAS04 is specifically isolated from crude human extracts by the present TFO approach. Indeed, when omitting the addition of TFO-1, the level of amplification of pAS04 is comparable with pAS03 as a negative control (FIG. 6C). The estimated signal to noise ratio is >20-fold (FIG. 6C).

It should be noted that in the present experiment, noise (i.e. the PCR signal generated by pAS03) is generated by DNA that represents 0.15% of total DNA. This amount is high compared to the situation involving a single copy of fragmented chromosomal DNA.

In CoIFI experiments, the difference between signal and noise will thus be much larger. Data show that the amount of noise is caused by the non-specific binding of DNA/protein complexes bound tightly on the surface of magnetic beads (-TFO experiments in FIG. 6C). Compared to the in vitro reaction in which 20 μg of C1 have the capacity to capture around 94 ng of pAS04, in the present human cell crude extract, 20 μg of C1 capture only around 0.1 ng of pAS04.

The present results show that the TFO approach is highly specific to capture TFT-1 target containing DNA even in the presence of large amount of non-target bulk DNA. The reduced recovery yield (≈2%) can be compensated by a corresponding increase in the amount of C1 beads.

The invention claimed is:

1. A method for the isolation of the proteins bound to a nucleic acid sequence of interest (Sequence-of-Interest: SoI), comprising:
   in a first step, introducing an exogenous Triplex Forming Tag sequence (TFT sequence) into said nucleic acid sequence of a living cell and growing said living cells;
   in a second step, collecting cells obtained in the first step and mixing with a molecular probe specific for the introduced TFT sequence (the TFO probe) under conditions that permit the formation of a nucleic acid triplex;
   in a third step, isolating the nucleic acid triplex formed in the second step, and analyzing the proteins that are bound to the SoI.

2. The method according to claim 1, wherein said nucleic acid sequence of interest (SoI) is genomic or episomal nucleic acid.

3. The method according to claim 2, wherein the SoI is genomic or episomal DNA.

4. The method according to claim 1, wherein said TFT sequence is a sequence that is not present in the nucleic acid sequence in which the SoI is present.

5. The method according to claim 1, wherein said TFT sequence is a poly-pyrimidine-poly-purine sequence.

6. The method according to claim 1, wherein said TFT sequence is a short triplex forming Tags sequence (TFT sequence) having a length comprised between 10 to 50 base pairs.

7. The method according to claim 1, wherein the second step further comprises performing cell fragmentation when the cells obtained in the first step are collected but before mixing with the TFO probe.

8. The method according to claim 1, wherein the second step further comprises purifying or isolating nuclei of the collected cells before adding the TFO-probe.

9. The method according to claim 1, further comprising cross-linking the proteins bound to the SoI.

10. The method according to claim 9, wherein the cross-linking is performed just after the first step but before the second step of collecting the cells.

11. The method according to claim 9, wherein the cross-linking is performed in the second step just after collecting the cells but before mixing with the TFO probe.

12. The method according to claim 9, wherein the cross-linking is performed using a method selected from the group consisting of UV photo crosslinking, formaldehyde cross-linking technique, Hexavalent chromium dimethyl adipimidate (DMA), disuccinimidyl suberate (D88), dithiobis[succinimidyl propionate] (D8P), and ethylene glycolbis [succinimidyl succinate] (EG8).

13. The method according to claim 9, further comprising performing a step of cell lysis either before or after the cross-linking of proteins bound to the SoI.

14. The method according to claim 9, further comprising performing a step of cell lysis before the cross-linking of proteins bound to SoI.

15. The method according to claim 1, further comprising performing a step of cell lysis.

16. The method according to claim 15, wherein the cell lysis step is performed once the cells have been collected in the second step.

17. The method according to claim 1, wherein said TFO probe is a nucleic acid sequence that is complementary to the inserted TFT.

18. The method according to claim 1, wherein said TFO probe is a nucleic acid sequence comprising locked nucleic acid (LNA) nucleotides.

19. The method according to claim 1, wherein, in said TFO, cytosines are replaced by 5-methyl cytosine.

20. The method according to claim 1, wherein said TFO comprises at its 3' or 5'-end an aromatic ring structure-containing compound capable of being intercalated into a double stranded TFT.

21. The method according to claim 20, wherein the aromatic ring structure-containing compound is selected from the group consisting of psoralen, acridine, ethidium bromide, berberine, proflavine, daunomycin, doxorubicin, thalidomide, quinacrine, and orthophenanthroline.

22. The method according to claim 20, wherein said TFO probe comprising an aromatic ring structure-containing compound at its 3' or 5'-end further comprises at its opposite end (3' or 5' end) a linker connected to a capture handle capable of being specifically captured by a cognate capture hook, said capture handle and cognate capture hook being molecules that interact or bind to one another.

23. The method according to claim 22, wherein said linker is a carbon spacer that can have a length comprised between 1 to 300 carbon atoms.

24. The method according to claim 22, wherein said cognate capture hook is streptavidin or Avidin or Neutravidin and said capture handle is biotin or desthiobiotin.

25. The method according to claim 24, wherein said cognate capture hook is fixed on a column or on beads.

26. The method according to claim 1, wherein said TFO is a nucleic acid sequence comprising locked nucleic acids (LNA) nucleotides that comprise at its 3' or 5'-end an aromatic ring structure-containing compound capable of being intercalated into a double stranded TFT.

27. The method according to claim 26, wherein cytosines in said nucleic acid sequence of said TFO is replaced with 5-methyl cytosine.

28. A kit for the implementation of the method according to claim 1, said kit comprising at least one TFT to be introduced near the SoI in the nucleic acid sequence of a living cell, at least one cross-linking compound, at least one molecular probe specific for the TFT (TFO) having a capture handle, and a cognate capture hook constituted by a compound that can bind to the capture handle of the TFO.

29. The method according to claim 1, wherein the TFT is a double stranded DNA capable of forming a triple helix with the TFO probe and capable of being introduced into a nucleic acid comprising the SoI so as to be positioned in close proximity to the SoI and the proteins that are bound to the SoI.

\* \* \* \* \*

SEQUENCE LISTING

```
<160> NUMBER OF SEQ ID NOS: 2

<210> SEQ ID NO 1
<211> LENGTH: 22
<212> TYPE: DNA
<213> ORGANISM: Artifical Sequence
<220> FEATURE:
<223> OTHER INFORMATION: Synthetic Triplex forming tag sequence

<400> SEQUENCE: 1
ttttcttttc tcctcttctc ct                                              22

<210> SEQ ID NO 2
<211> LENGTH: 22
<212> TYPE: DNA
<213> ORGANISM: Artifical Sequence
<220> FEATURE:
<223> OTHER INFORMATION: Synthetic Triplex forming tag sequence

<400> SEQUENCE: 2
aaaagaaaag aggagaagag ga                                              22
```